United States Patent
Olczak et al.

(10) Patent No.: US 7,336,370 B1
(45) Date of Patent: Feb. 26, 2008

(54) OPTICAL NULLING APPARATUS AND METHOD FOR TESTING AN OPTICAL SURFACE

(75) Inventors: Eugene Olczak, Pittsford, NY (US); John J. Hannon, Rochester, NY (US); Thomas W. Dey, Springwater, NY (US); Arthur E. Jensen, Rochester, NY (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 118 days.

(21) Appl. No.: 11/268,014

(22) Filed: Nov. 7, 2005

Related U.S. Application Data

(60) Provisional application No. 60/705,694, filed on Aug. 4, 2005.

(51) Int. Cl.
*G01B 9/02* (2006.01)
(52) U.S. Cl. ...................... 356/512; 356/124
(58) Field of Classification Search ........ 365/512–515, 365/124
See application file for complete search history.

(56) References Cited

U.S. PATENT DOCUMENTS 4,958,931 A * 9/1990 Tatian ..................... 356/513
6,624,895 B1 * 9/2003 Moriyasu et al. .......... 356/513
2005/0275849 A1 * 12/2005 Freimann et al. ......... 356/521

OTHER PUBLICATIONS

Daniel Malacara, "Optical Shop Testing", Second Edition, John Wiley & Sons, Inc., 1992, pp. 438-442; pp. 755-762.

* cited by examiner

*Primary Examiner*—Samuel A. Turner
(74) *Attorney, Agent, or Firm*—RatnerPrestia

(57) ABSTRACT

An optical nulling apparatus for testing an optical surface includes an aspheric mirror having a reflecting surface for imaging light near or onto the optical surface under test, where the aspheric mirror is configured to reduce spherical aberration of the optical surface under test. The apparatus includes a light source for emitting light toward the aspheric mirror, the light source longitudinally aligned with the aspheric mirror and the optical surface under test. The aspheric mirror is disposed between the light source and the optical surface under test, and the emitted light is reflected off the reflecting surface of the aspheric mirror and imaged near or onto the optical surface under test. An optical measuring device is disposed between the light source and the aspheric mirror, where light reflected from the optical surface under test enters the optical measuring device. An imaging mirror is disposed longitudinally between the light source and the aspheric mirror, and the imaging mirror is configured to again reflect light, which is first reflected from the reflecting surface of the aspheric mirror, onto the optical surface under test.

16 Claims, 4 Drawing Sheets

RMS WAVEFRONT ERROR VS WAVELENGTH

CATADIOPTRIC OFFNER

CATOPTRIC ASPHERE

OPTICAL NULLING APPARATUS AND METHOD FOR TESTING AN OPTICAL SURFACE

CROSS REFERENCE TO RELATED APPLICATIONS

This application claims priority of U.S. Provisional Patent Application Ser. No. 60/705,694, filed Aug. 4, 2005.

STATEMENT REGARDING FEDERALLY SPONSORED RESEARCH

The invention described herein was made in the performance of work under NASA Contract No. NAS5-02200 and is subject to the provisions of Section 305 of the National Aeronautics and Space Act of 1958 (42 U.S.C. 2457).

FIELD OF THE INVENTION

The disclosure is in the field of optics. More specifically, it is in the field of optical testing of large optical surfaces.

BACKGROUND OF THE INVENTION

A null lens is commonly used in testing an optical surface (test surface). One example of its use is testing a large concave parabolic optical surface using an optical interferometer. It is convenient to test the optical surface using a diverging beam of light originating near the center of curvature of the surface. Unfortunately, the test surface does not return a well-corrected wavefront at this conjugate. Typically, large amounts of spherical aberration are present in the wavefront even when the test surface is of high quality.

The null lens is used to compensate for this wavefront error by providing a calibrated correction to the expected aberrations in the optical surface to be tested. A reflective Offner null is typically used in this case. (See, e.g., *Optical Shop Testing*, Second Edition, D. Malacara, ed., John Wiley & Sons, Inc., 1992, pp. 440.)

The Offner null requires two large low F-number spherical mirrors that are difficult to fabricate. It may also include a field lens, which makes it catadioptric—containing both mirrors and lenses. A field lens can introduce chromatic aberration, which results in extra wavefront distortion that changes with the wavelength of the light used to interrogate the surface. The Offner assembly is also relatively sensitive to tilt of the surface to be tested (hereafter referred to as field of view) and temperature variations of the assembly.

Because of the low F-number of the mirror surfaces included in the Offner assembly, an objective lens with a high numerical aperture is required to inject light into the test assembly. Such an objective lens is difficult to fabricate, calibrate, and align.

Many all-reflective (catoptric) null test assemblies require reflecting surfaces which are large relative to the size of the surface under test. These include full-aperture autocollimation flats (for testing concave paraboloidal mirrors from their focii, or testing complete telescope systems), and large spherical mirrors (for "Hindle" and "Ritchey Common" tests). In the autocollimation flat assembly, the flat mirror must be at least as big as the mirror under test. In assemblies using a single large concave spherical reflector to null the aberrated wavefront of a concave paraboloid, it is not possible to completely null the wavefront without making the reflector aspherical. The reflector also has to be about one-third the diameter of the mirror under test. If the mirror under test is, for example, a large primary telescope mirror exceeding 5 meters in diameter, the large mirrors required for the null assembly are difficult and expensive to fabricate and difficult to support mechanically. (See Malacara, Appendix 2.)

Embodiments of the present invention overcome these limitations by including a relatively small aspheric mirror in conjunction with a second small mirror to provide a nearly perfect nulling function. Additional optics provide proper imaging. The correction is contained on the aspheric mirror, making these additional optics relatively simple to fabricate and align. Sensitivity to figure errors in the aspheric mirror is reduced and the field of view of the null is increased compared to an Offner null designed for an equivalent test. Embodiments of the present invention for testing a mirror 6 meters in diameter have no mirrors with a diameter exceeding 0.3 meters included in the null assembly. These same embodiments employ a focus feed with an f-number no less than 3.3, as contrasted with the very fast speed (f~1.25) needed for the autocollimation test configuration.

SUMMARY OF THE INVENTION

To meet this and other needs, and in view of its purposes, the present invention provides an optical nulling apparatus for testing an optical surface. The nulling apparatus includes an aspheric mirror having a reflecting surface for reflecting light near or onto the optical surface under test, where the aspheric mirror is configured to reduce aberration of the optical surface under test. A light source is included for emitting light toward the aspheric mirror, the light source longitudinally aligned with the aspheric mirror and the optical surface under test. The aspheric mirror is disposed between the light source and the optical surface under tests. The apparatus includes an imaging mirror disposed longitudinally between the light source and the aspheric mirror. The emitted light is reflected off the reflecting surface of the aspheric mirror. The imaging mirror is configured to again reflect the light, which was first reflected from the reflecting surface of the aspheric mirror, onto the optical surface under test. In addition, an optical measuring device is disposed between the light source and the aspheric mirror. Light reflected from the optical surface under test enters the optical measuring device. Collimating optics may be disposed between the light source and the aspheric mirror. The collimating optics collimate the light from the light source toward the aspheric mirror.

The light source, the optical measuring device, the collimating optics, the imaging mirror and the aspheric mirror are longitudinally aligned to the optical surface under test. Each is positioned, respectively, in a sequence having the light source furthest from the optical surface under test, and the aspheric mirror closest to the optical surface under test. The imaging mirror includes a first aperture for passing light from the light source onto the reflecting surface of the aspheric mirror. A reflecting surface of the imaging mirror and the reflecting surface of the aspheric mirror are disposed facing each other, and configured to reflect the passed light from the surface of the aspheric mirror toward the surface of the imaging mirror, and then from the surface the imaging mirror toward the optical surface under test. The aspheric mirror includes a second aperture for passing light reflected from the surface of the imaging mirror toward the optical surface under test. The light propagating between the light source and the optical surface under test is configured to encounter optical surfaces that are catoptric. The reflecting surface of the aspheric mirror has a shape that is based on an ideal shape of the optical surface under test, and described mathematically as a rotationally symmetric polynomial aspheric surface.

Another embodiment of the present invention includes a method for testing an optical surface including forming an optical wavefront using an apparatus having an imaging mirror and an aspheric mirror facing each other, each having first and second apertures, respectively, for receiving light from a light source and transmitting light to the optical surface under test. The method further includes calculating shape of a surface of the aspheric mirror based on shape of the optical surface under test, and causing interference between light transmitted to the optical surface under test and light reflected from the optical surface.

The method further includes the steps of: (a) focusing light from the light source toward the first aperture; (b) reflecting light from a surface of the imaging mirror toward the second aperture of the aspheric mirror; (c) calculating a holographic pattern from shape of the optical surface under test, fabricating a hologram from the holographic pattern, and calibrating the apparatus using the hologram.

Another embodiment of the invention includes a method having the steps of: (a) directing light from a light source, through a first aperture of an imaging mirror, toward an aspheric mirror, (b) reflecting light from a surface of the aspheric mirror onto a surface of the imaging mirror, (c) reflecting light from the surface of the imaging mirror through a second aperture of the aspheric mirror, and (d) impinging light onto the optical surface under test. The method may further include the steps of: (e) reflecting light from the optical surface under test, through the second aperture, toward the surface of the imaging mirror, (f) reflecting light from the surface of the imaging mirror toward the surface of the aspheric mirror, and (g) reflecting light from the surface of the aspheric mirror through the first aperture, toward an optical measuring device.

It is understood that the foregoing general description and the following detailed description are exemplary, but are not restrictive, of the invention.

DETAILED DESCRIPTION OF THE INVENTION

Figure 1:
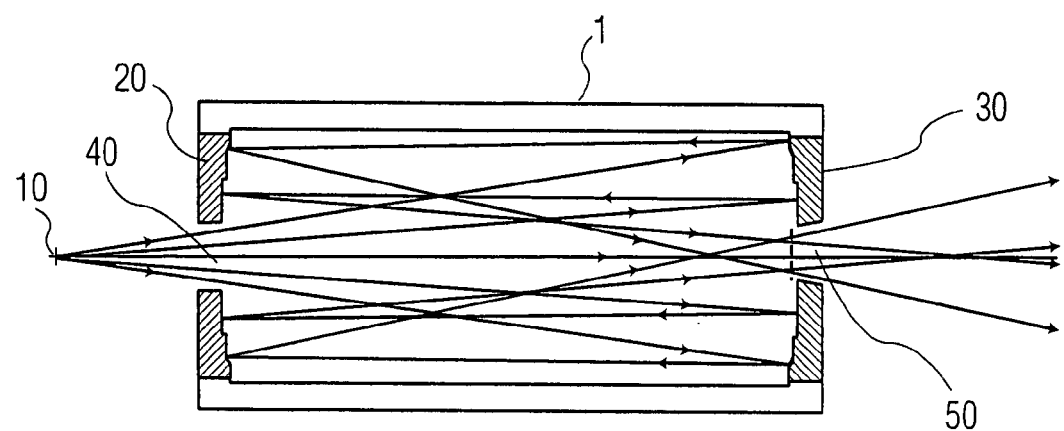
FIG. 1 shows one embodiment of a nulling apparatus of the present invention for testing an optical surface, including an aspheric mirror, and a spherical imaging mirror.

FIG. 1 shows one embodiment of nulling apparatus 1 for testing an optical surface, such as the reflecting surface of a primary mirror of a telescope. Nulling apparatus 1 includes aspheric mirror 30, and spherical imaging mirror 20. The spherical imaging mirror 20 images the reflecting surface of aspheric mirror 30 either near or onto the optical surface to be tested (not shown). Spherical imaging mirror 20 is disposed between a light source (not shown) and aspheric mirror 30. Aspheric mirror 30 is disposed between spherical imaging mirror 20 and the optical surface.

In this embodiment, light from the light source is focused to focal point 10. Light rays diverging from focal point 10 enter through hole 40 in spherical mirror 20. Most of the rays from focal point 10, after passing through hole 40 in spherical imaging mirror 20, reflect off the surface of aspheric mirror 30, and travel back to spherical mirror 20. The rays are then reflected in the other direction through hole 50 in aspheric mirror 30, eventually reaching the surface to be tested.

After reflecting from the surface to be tested, the rays re-enter apparatus 1 by passing through hole 50 in aspheric mirror 30, reflect from spherical imaging mirror 20 and then reflect from aspheric mirror 30 to pass through hole 40 for further processing.

The reflecting surface of the aspheric mirror 30 has a shape based on an ideal shape of the optical surface. The shape of the reflecting surface of the aspheric mirror 30 may be calculated, based on an ideal shape of the optical surface. The ideal shape of the optical surface to be tested, in turn, may be described mathematically as a rotationally symmetric polynomial aspheric surface. Such surfaces may be modeled with an equation containing a polynomial expansion of the deviation of a spherical or conic surface from an ideal surface. An example of such an equation is an even asphere surface model, which uses the even powers of the radial coordinate to describe the aconicity of a surface. The equation is as follows:

$$z = \frac{cr^2}{1 + \sqrt{1 - (1+k)c^2 r^2}} + \alpha_1 r^2 + \alpha_2 r^4 + \\ \alpha_3 r^6 + \alpha_4 r^8 + \alpha_5 r^{10} + \alpha_6 r^{12} + \alpha_7 r^{14} + \alpha_8 r^{16}. \quad (1)$$

In this equation, z is the deviation, or sag, from the vertex tangent plane, of the surface as a function of a radial coordinate r. The symbol c is the reciprocal of the base radius of curvature, k is the conic constant and $\alpha_1$ through $\alpha_8$ are fitting coefficients. The conic constant k determines the nature of the conic surface; for example, hyperbola for k<−1, parabola for k=−1, ellipse for −1<k<0, and sphere for k=0.

The calculation of the aspheric surface may be carried out using known optical design software, such as ZEMAX. Various design constraints may be used in the calculation to realize desired advantages. One example of such a constraint is to require that the smallest possible central perforation of the reflecting surface of aspheric mirror 30 pass all test rays joining spherical imaging mirror 20 and the surface to be tested. This condition assures that no vignetting of the test rays will occur and that nulling apparatus 1 is compact. Such constraint is equivalent to locating the reflecting surface of aspheric mirror 30 at the beam waist of the ray caustic.

An example of a design prescription used as input in such calculations is appended as Appendix A. An example of a computed aspheric surface is appended as Appendix B.

Results of Equation (1) may be used to fabricate aspheric surface 30 to the desired shape using known techniques in the art, such as computer-controlled grinding and polishing or single point diamond turning.

Figure 2:
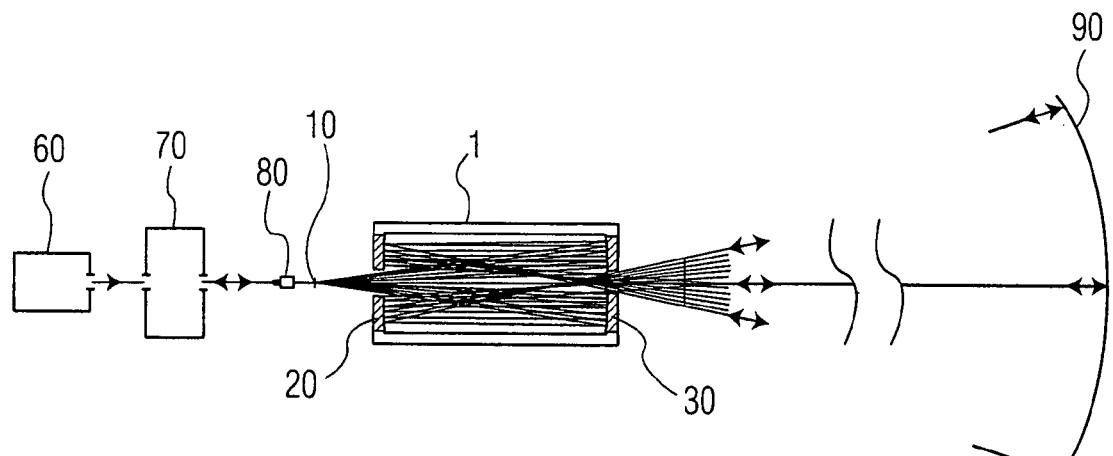
FIG. 2 shows an embodiment of a system for testing an optical surface which includes the nulling apparatus shown in FIG. 1.

FIG. 2 shows an embodiment of a system for testing an optical surface which includes nulling apparatus 1. In this embodiment, light from light source 60, such as a laser, enters an optical measuring device 70 such as an interferometer. Light emerging from the optical measuring device 70 is collimated and focused to focal point 10 by focusing optics 80, which may include a focusing mirror or an objective lens. After being focused, the light propagates through apparatus 1 and then impinges onto surface 90 which is under test. After reflecting from surface 90, the light propagates through apparatus 1 and eventually re-enters optical measuring device 70. If optical measuring device 70 is an interferometer, light from the light source 60 and light reflected from the optical surface interfere with each other within the interferometer. The resulting interference pattern provides a map of deviations in surface 90 from the desired ideal surface.

Alternative embodiments may have light from the light source 60 entering the apparatus 1 or focusing optics 80 not through the optical measuring device 70 but instead through some other means. Such means may include an additional focusing optic and other optical apparatus such as beam splitters or mirrors. In this case the light reflected from surface 90 may also enter the optical measuring device 70 as in FIG. 2. For example the optical measuring device 70 may be a wavefront shearing interferometer, a Shack-Hartmann wavefront sensor, phase diversity sensor or any other single pass optical measuring device. Alternately the system may comprise a plurality of test instruments that may or may not have common use of apparatus 1, light source 60 or focusing optics 80.

The system of FIG. 2 may be calibrated without a physical optical surface 90, using a mathematical description of the optical surface. From the mathematical description (such as described above), a holographic pattern is calculated. The resulting holographic pattern, in mathematical form, is then used to fabricate a physical hologram using known techniques. This physical hologram is then used in place of optical surface 90 to calibrate the system. The physical hologram may be positioned between apparatus 1 and the expected position of optical surface 90. If the physical hologram is positioned much closer to the apparatus 1 than to the expected position of optical surface 90, the size of the hologram can be made relatively compact. For example, a reflective hologram designed to calibrate the nulling apparatus for testing a mirror 6 meters in diameter may be less than 150 mm in diameter.

The focusing element 80 may be any optical system capable of producing focal point 10. In one particular embodiment, focusing optics 80 may include an objective lens. Ideally, the entire optical system is achromatic, or as nearly so as possible. Because the system does not have elements with any appreciable chromatic dispersion, nulling apparatus 1 and optical measuring device 70 may use white light, multi-spectral light, multi-wavelength light, or broadband light, without degradation due to chromatic aberration or other forms of degradation in the interference pattern. In general any portion of the electromagnetic spectrum either in part or in whole may be used.

The optics of nulling apparatus 1 may be such that the light strikes is spherical mirror 20 in a relatively tight annular band. This allows focusing optics 80 to be pulled farther away from the spherical mirror, thus reducing the numerical aperture.

In a series of computer simulations, an embodiment of a catoptric asphere null apparatus of the present invention is compared with a conventional null apparatus, known in the art as a catadioptric Offner. (Offner-type null compensators are described in *Optical Shop Testing*, Second Edition, D. Malacara, ed., John Wiley & Sons, Inc., 1992, pp. 438 ff.) In this comparison, the optical surface under test is the same in both cases, namely a 6-meter diameter primary telescope mirror, with a surface vertex radius of 16 meters. The resulting f-number of this surface is 1.25, indicating a surface that is known in the art as "fast", or "highly curved", and, therefore, relatively difficult to test. The boundary conditions imposed on both nulling apparati are that each must transform a monochromatic or polychromatic collimated beam, emanating from an interferometer, into a highly corrected wavefront that complements the wavefront of a nominally-perfect primary mirror (PM), when viewed from the center of curvature.

In one simulation the wavefront error is determined at a monochromatic wavelength of 637 nm. The wavefront error in wavelength RMS equivalence of test surface is 0.00085 wavelength for the catadioptric Offner, but only 0.000025 wavelength for the catoptric asphere.

Figure 3A:
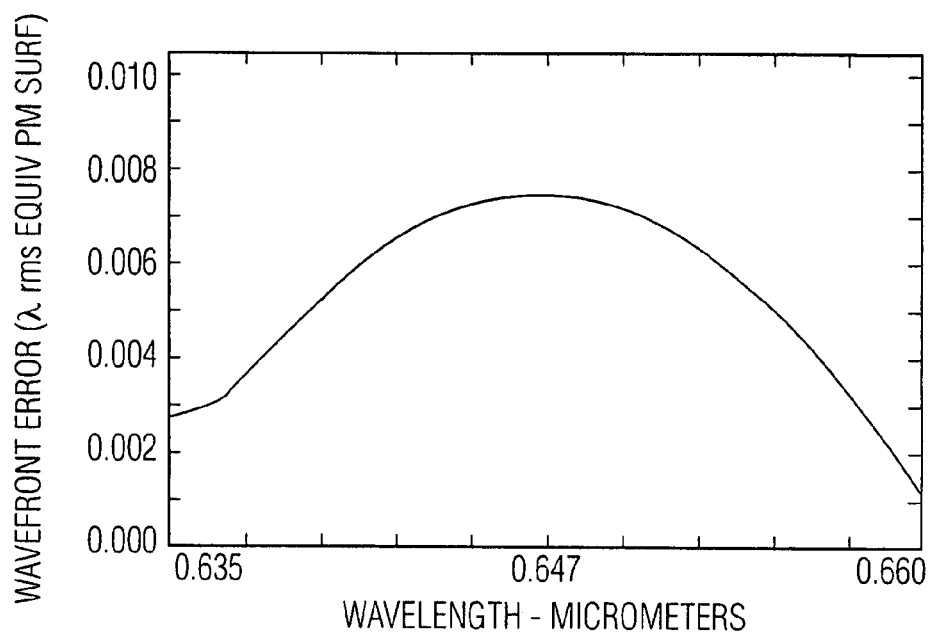
FIGS. 3A and 3B are plots showing the wavefront error of a catadioptric Offner apparatus (3A) and of an embodiment of the present invention (3B).
Figure 3B:
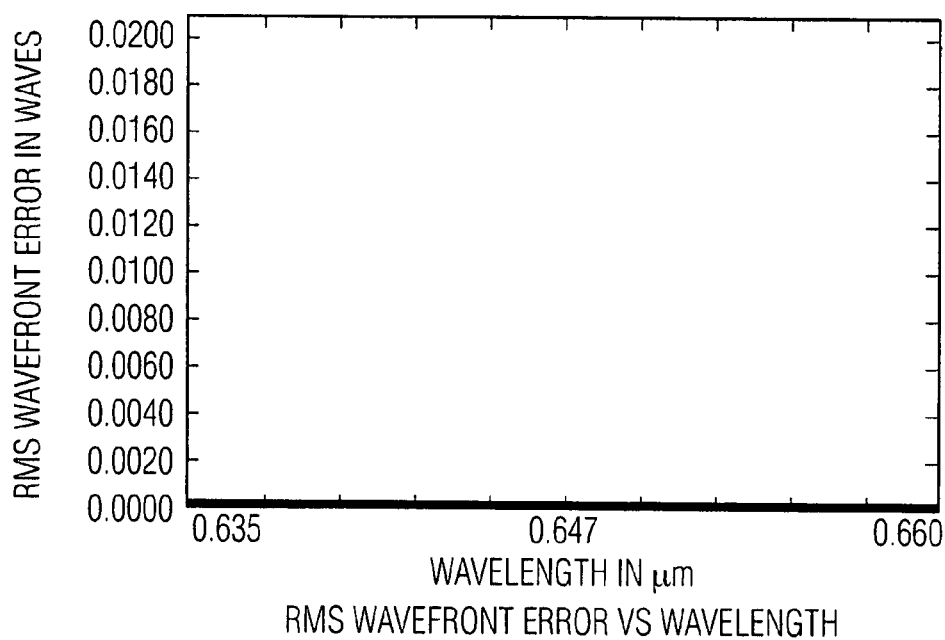

FIGS. 3-5 show further results of the simulations. FIG. 3A shows a plot of the wavefront error of the catadioptric Offner apparatus arising from chromatic aberration in the field lens. By contrast, FIG. 3B shows an equivalent plot for an embodiment of the present invention. As shown, the wavefront error at all wavelengths for an embodiment of the present invention is zero, because lenses or other chromatically dispersive optics are not used.

Figure 4A:
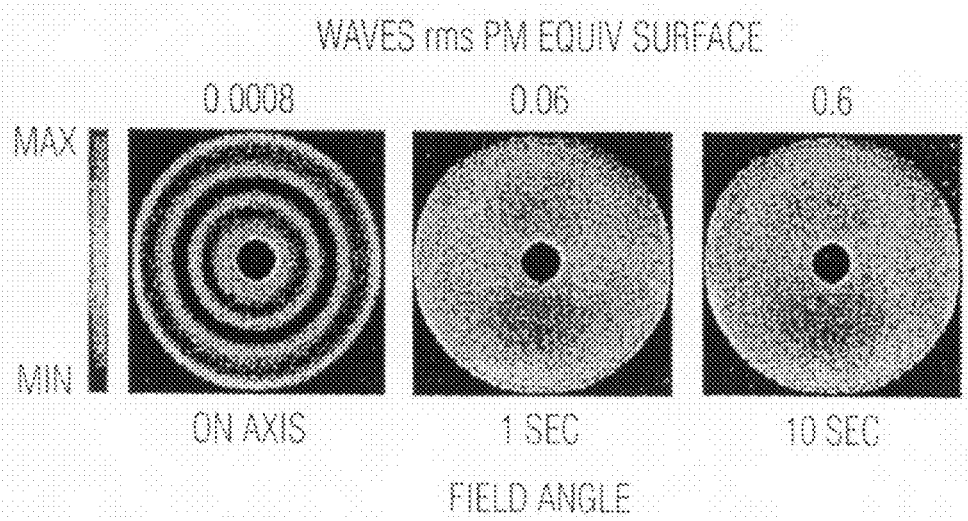
FIGS. 4A and 4B show a comparison between the fields of view of a catadioptric Offner apparatus (4A) and of an embodiment of the present invention (4B).
Figure 4B:
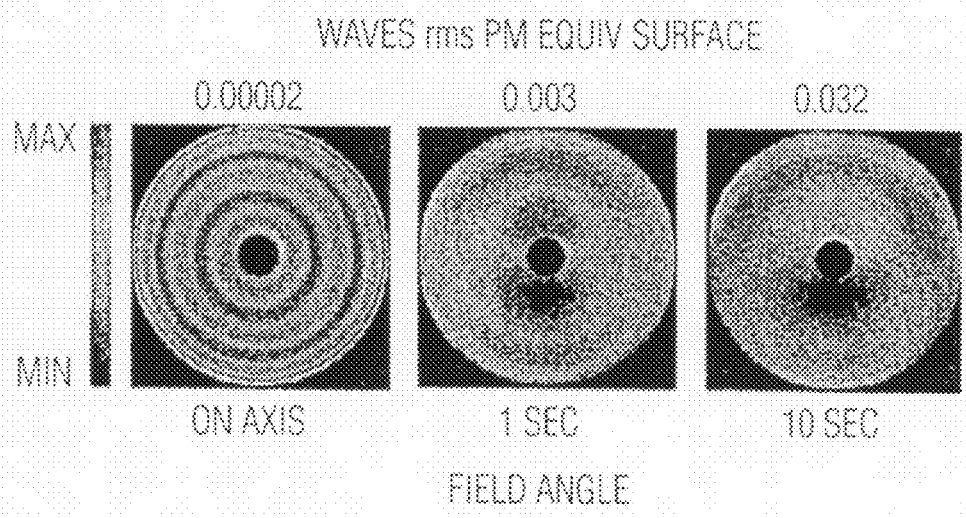

FIGS. 4A and 4B show a comparison between the fields of view of a catadioptric Offner (4A) and an embodiment of the present invention (4B). The wavefronts are shown being interrogated at half-fields of 0 (on-axis), 1, and 10 arc-seconds. The embodiment of the present invention (4B) is about 20 times less sensitive to off-axis tilt, as indicated by comparison of the wave's rms equivalent surface error for each angle.

Figure 5A:
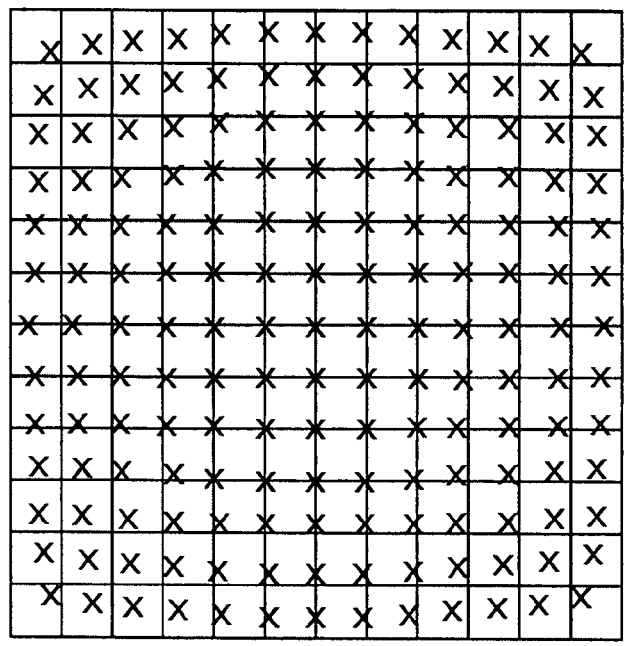
FIGS. 5A and 5B show the results of a computer simulation comparing the pupil distortions of a catadioptric Offner apparatus (5A) and of an embodiment of the present invention (5B).
Figure 5B:
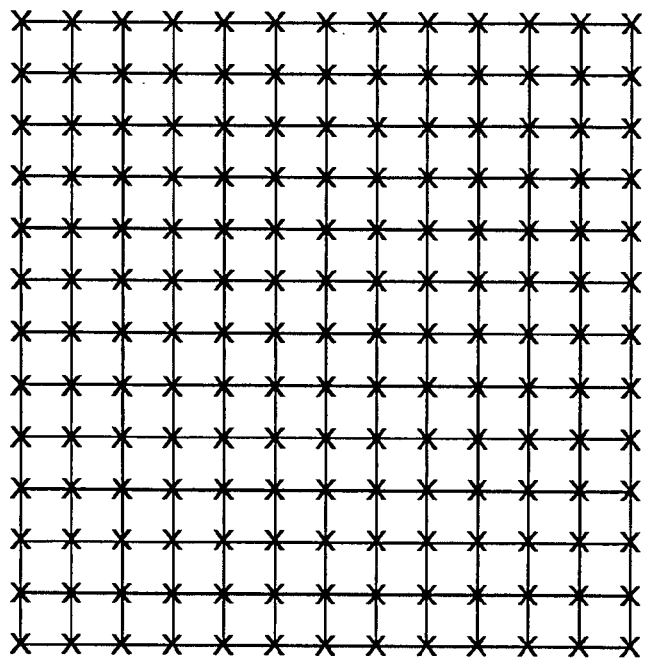

FIGS. 5A and 5B show the results of a computer simulation comparing the pupil distortions between the catadioptric Offner (5A) and an embodiment of the present invention (5B). The catadioptric Offner suffers significant "barrel" distortion. This distortion has to be corrected by carefully mapping, using software, the wavefront reflecting from the optical surface under test. By contrast, the embodiment of the present invention (5B) shows negligible distortion.

Although the present invention is illustrated and described herein with reference to specific embodiments, the invention is not intended to be limited to the details shown. Rather, various modifications may be made in the details within the scope and range of equivalents of the claims and without departing from the invention.

APPENDIX A

| System/Prescription Data | |
|---|---|
| GENERAL LENS DATA: | |
| Surfaces: | 18 |
| Stop: | 9 |
| System Aperture: | Float By Stop Size = 3298 |
| Glass Catalogs: | SCHOTT_2000 INFRARED |
| Ray Aiming: | Real Reference, Cache On |
| X Pupil shift: | 0 |
| Y Pupil shift: | 0 |

APPENDIX A-continued

| System/Prescription Data | |
|---|---|
| Z Pupil shift: | 0 |
| Apodization: | Uniform, factor = 0.00000E+000 |
| Effective Focal Length: | 410.9035 (in air at system temperature and pressure) |
| Effective Focal Length: | 410.9035 (in image space) |
| Back Focal Length: | 2547.112 |
| Total Track: | 16958.05 |
| Image Space F/#: | 1.672272 |
| Paraxial Working F/#: | 3.344281 |
| Working F/#: | 3.320915 |
| Image Space NA: | 0.1478655 |
| Object Space NA: | 0.1478427 |
| Stop Radius: | −3298 |
| Paraxial Image Height: | 0 |
| Paraxial Magnification: | 0 |
| Entrance Pupil Diameter: | 245.7157 |
| Entrance Pupil Position: | 641.8717 |
| Exit Pupil Diameter: | 245.7157 |
| Exit Pupil Position: | 821.8717 |
| Field Type: | Real Image height in Millimeters |
| Maximum Field: | 0 |
| Primary Wave: | 0.66 |
| Lens Units: | Millimeters |

SURFACE DATA SUMMARY:

| Surf | Type | Comment | Radius | Thickness | Glass | Diameter | Conic |
|---|---|---|---|---|---|---|---|
| OBJ | STANDARD | | Infinity | 180 | | 0.3219932 | 0 |
| 1 | STANDARD | | Infinity | 632.0481 | | 60.55108 | 0 |
| 2 | EVENASPH | | −4960.253 | −632.0481 | MIRROR | 270.7972 | 1138.615 |
| 3 | EVENASPH | | 1200 | 632.0481 | MIRROR | 248.6184 | 0 |
| 4 | EVENASPH | | −4960.253 | 60 | | 38.27344 | 1138.615 |
| 5 | TILTSURF | | — | 25 | F_SILICA | 100 | — |
| 6 | TILTSURF | | — | 8892 | | 100 | — |
| 7 | STANDARD | | Infinity | 7169 | | 4136.411 | 0 |
| 8 | COORDBRK | | — | 0 | | — | — |
| STO | STANDARD | | −15879.72 | −7169 | MIRROR | 6596 | −0.9966605 |
| 10 | COORDBRK | | — | 0 | | — | — |
| 11 | STANDARD | | Infinity | −8892 | | 4136.295 | 0 |
| 12 | TILTSURF | | — | −25 | F_SILICA | 50 | — |
| 13 | TILTSURF | | — | −60 | | 50 | — |
| 14 | EVENASPH | | −4960.253 | −632.0481 | | 37.89827 | 1138.615 |
| 15 | EVENASPH | | 1200 | 632.0481 | MIRROR | 248.4688 | 0 |
| 16 | EVENASPH | | −4960.253 | −632.0481 | MIRROR | 270.7969 | 1138.615 |
| 17 | STANDARD | | Infinity | −180 | | 60.15499 | 0 |
| IMA | STANDARD | | Infinity | | | 0.1428695 | 0 |

SURFACE DATA DETAIL:

| | |
|---|---|
| Surface OBJ: | STANDARD |
| Surface 1: | STANDARD |
| Surface 2: | EVENASPH |
| Coeff on r 2: | 0 |
| Coeff on r 4: | −7.2159924e−009 |
| Coeff on r 6: | 4.9833759e−014 |
| Coeff on r 8: | 3.0410497e−018 |
| Coeff on r 10: | −4.3825723e−022 |
| Coeff on r 12: | 4.3343695e−026 |
| Coeff on r 14: | −2.0617546e−030 |
| Coeff on r 16: | 4.6517737e−035 |
| Surface 3: | EVENASPH |
| Coeff on r 2: | 0 |
| Coeff on r 4: | 0 |
| Coeff on r 6: | 0 |
| Coeff on r 8: | 0 |
| Coeff on r 10: | 0 |
| Coeff on r 12: | 0 |
| Coeff on r 14: | 0 |
| Coeff on r 16: | 0 |
| Surface 4: | EVENASPH |
| Coeff on r 2: | 0 |
| Coeff on r 4: | −7.2159924e−009 |
| Coeff on r 6: | 4.9833759e−014 |
| Coeff on r 8: | 3.0410497e−018 |
| Coeff on r 10: | −4.3825723e−022 |
| Coeff on r 12: | 4.3343695e−026 |
| Coeff on r 14: | −2.0617546e−030 |

APPENDIX A-continued

| System/Prescription Data | |
|---|---|
| Coeff on r 16: | 4.6517737e−035 |
| Aperture: | Circular Aperture |
| Minimum Radius: | 0 |
| Maximum Radius: | 19 |
| Surface 5: | TILTSURF |
| X Tangent: | 0 |
| Y Tangent: | 0 |
| Aperture: | Floating Aperture |
| Maximum Radius: | 50 |
| Surface 6: | TILTSURF |
| X Tangent: | 0 |
| Y Tangent: | 0 |
| Aperture: | Floating Aperture |
| Maximum Radius: | 50 |
| Surface 7: | STANDARD |
| Surface 8: | COORDBRK |
| Decenter X: | 0 |
| Decenter Y: | 0 |
| Tilt About X: | 0.00027 |
| Tilt About Y: | 0 |
| Tilt About Z: | 0 |
| Order: | Decenter then tilt |
| Surface STO: | STANDARD |
| Aperture: | Circular Aperture |
| Minimum Radius: | 500 |
| Maximum Radius: | 3300 |
| Surface 10: | COORDBRK |
| Decenter X: | 0 |
| Decenter Y: | 0 |
| Tilt About X: | −0.00027 |
| Tilt About Y: | 0 |
| Tilt About Z: | 0 |
| Order: | Decenter then tilt |
| Surface 11: | STANDARD |
| Surface 12: | TILTSURF |
| X Tangent: | 0 |
| Y Tangent: | 0 |
| Aperture: | Floating Aperture |
| Maximum Radius: | 25 |
| Surface 13: | TILTSURF |
| X Tangent: | 0 |
| Y Tangent: | 0 |
| Aperture: | Floating Aperture |
| Maximum Radius: | 25 |
| Surface 14: | EVENASPH |
| Coeff on r 2: | 0 |
| Coeff on r 4: | −7.2159924e−009 |
| Coeff on r 6: | 4.9833759e−014 |
| Coeff on r 8: | 3.0410497e−018 |
| Coeff on r 10: | −4.3825723e−022 |
| Coeff on r 12: | 4.3343695e−026 |
| Coeff on r 14: | −2.0617546e−030 |
| Coeff on r 16: | 4.6517737e−035 |
| Surface 15: | EVENASPH |
| Coeff on r 2: | 0 |
| Coeff on r 4: | 0 |
| Coeff on r 6: | 0 |
| Coeff on r 8: | 0 |
| Coeff on r 10: | 0 |
| Coeff on r 12: | 0 |
| Coeff on r 14: | 0 |
| Coeff on r 16: | 0 |
| Surface 16: | EVENASPH |
| Coeff on r 2: | 0 |
| Coeff on r 4: | −7.2159924e−009 |
| Coeff on r 6: | 4.9833759e−014 |
| Coeff on r 8: | 3.0410497e−018 |
| Coeff on r 10: | −4.3825723e−022 |
| Coeff on r 12: | 4.3343695e−026 |
| Coeff on r 14: | −2.0617546e−030 |
| Coeff on r 16: | 4.6517737e−035 |
| Surface 17: | STANDARD |
| Surface IMA: | STANDARD |

APPENDIX B

CONVEX EVEN ASPHERE MIRROR

Dimensions in millimeters

| | |
|---|---|
| Radius of Curvature | −4309.5305 |
| Conic Constant | −761.6141 |
| Coeff on r 2: | 0 |
| Coeff on r 4: | −9.3960734e−009 |
| Coeff on r 6: | 5.071379e−014 |
| Coeff on r 8: | −1.2841665e−018 |
| Coeff on r 10: | 1.80173e−023 |
| Coeff on r 12: | −7.4593527e−029 (may be able to trim this term in the future) |

Even Asphere

Rotationally symmetric polynomial aspheric surfaces are described by a polynomial expansion of the deviation from a spherical (or aspheric described by a conic) surface. The even asphere surface model uses only the even powers of the radial coordinate to describe the asphericity. The model uses the base radius of curvature and the conic constant. The surface sag is given by $$z = \frac{cr^2}{1+\sqrt{1-(1+k)c^2r^2}} + \alpha_1 r^2 + \alpha_2 r^4 + \alpha_3 r^6 + \alpha_4 r^8 + \alpha_5 r^{10} + \alpha_6 r^{12} + \alpha_7 r^{14} + \alpha_8 r^{16}.$$

where:
  c = reciprocal of the base radius of curvature
  k = conic constant

| | |
|---|---|
| Aperture: | Circular Aperture |
| Minimum Aperture Radius: | 20 |
| Maximum Aperture Radius: | 135.4746 |

What is claimed is:

1. An optical nulling apparatus for testing an optical surface comprising
   an aspheric mirror having a reflecting surface for reflecting light configured to reduce aberration of the optical surface under test;
   a light source for emitting light toward the aspheric mirror;
   an imaging mirror disposed longitudinally between the light source and the aspheric mirror, and
   the imaging mirror configured to again reflect light, which is first reflected from the reflecting surface of the aspheric mirror, onto the optical surface under test.

2. The apparatus of claim 1, wherein
   the light source is longitudinally aligned with the aspheric mirror and the optical surface under test, and
   the aspheric mirror is disposed between the light source and the optical surface under test, and
   the emitted light is reflected off the reflecting surface of the aspheric mirror and imaged near or onto the optical surface under test.

3. The apparatus of claim 2, including
   an optical measuring device disposed between the light source and the aspheric mirror,
   wherein light reflected from the optical surface under test enters the optical measuring device.

4. The apparatus of claim 2, including
   collimating optics disposed between the light source and the aspheric mirror,
   wherein the collimating optics collimates the light from the light source toward the aspheric mirror.

5. The apparatus of claim 1, wherein
   the imaging mirror is spherical in shape.

6. The apparatus of claim 1, wherein
   the light source, the imaging mirror and the aspheric mirror are longitudinally aligned to the optical surface under test, and
   each is positioned, respectively, in a sequence having the light source furthest from the optical surface under test, and the aspheric mirror closest to the optical surface under test.

7. The apparatus of claim 1, wherein
   the imaging mirror includes a first aperture for passing light from the light source onto the reflecting surface of the aspheric mirror, and
   a reflecting surface of the imaging mirror and the reflecting surface of the aspheric mirror are disposed facing each other, and configured to reflect the passed light from the surface of the aspheric mirror toward the surface of the imaging mirror, and then from the surface the imaging mirror toward the optical surface under test.

8. The apparatus of claim 7, wherein
   the aspheric mirror includes a second aperture for passing light reflected from the surface of the imaging mirror toward the optical surface under test.

9. The apparatus of claim 1, wherein
   the reflecting surface of the aspheric mirror has a shape based on an ideal shape of the optical surface under test, and
   the ideal shape is described mathematically as a rotationally symmetric polynomial aspheric surface.

10. A method of testing an optical surface comprising the steps of:
    directing light from a light source, through a first aperture of an imaging mirror, toward an aspheric mirror,
    reflecting light from a surface of the aspheric mirror onto a surface of the imaging mirror,
    reflecting light from the surface of the imaging mirror through a second aperture of the aspheric mirror, and
    impinging light onto the optical surface under test.

11. The method of claim 10, further including the steps of:
    reflecting light from the optical surface under test, through the second aperture, toward the surface of the imaging mirror,
    reflecting light from the surface of the imaging mirror toward the surface of the aspheric mirror, and
    reflecting light from the surface of the aspheric mirror through the first aperture, toward an optical measuring device.

12. An optical nulling apparatus for testing an optical surface comprising
    a light source for emitting light in a path,
    an imaging mirror disposed in the path of the light,
    an aspheric mirror disposed in the path of the light, and
    the light source, the imaging mirror, the aspheric mirror and an optical surface under test are sequentially positioned in the path of the light,
    wherein the aspheric mirror is configured to reflect light toward the imaging mirror, and the imaging mirror is configured to reflect light toward the optical surface under test.

13. The apparatus of claim 12 wherein
    the imaging mirror includes a first aperture for passing light from the light source onto a reflecting surface of the aspheric mirror.

14. The apparatus of claim 13 wherein
the aspheric mirror includes a second aperture for passing light reflected from a surface of the imaging mirror toward the optical surface under test.

15. The apparatus of claim 12 wherein
a reflecting surface of the aspheric mirror has a shape based on an ideal shape of the optical surface under test, and
the ideal shape is described mathematically as a rotationally symmetric polynomial aspheric surface.

16. The apparatus of claim 15 including
an optical measuring device, disposed in the path of the light, for providing a map of deviations in the optical surface under test from the ideal shape.

* * * * *